United States Patent
Korn et al.

(10) Patent No.: US 7,629,126 B2
(45) Date of Patent: Dec. 8, 2009

(54) PIM-3 KINASE AS A TARGET FOR TYPE 2 DIABETES MELLITUS

(75) Inventors: Marc Korn, Offenbach (DE); Guenter Mueller, Sulzbach (DE); Rudolf Schneider, Niedernhausen (DE); Georg Tschank, Essenheim (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 148 days.

(21) Appl. No.: 11/609,652

(22) Filed: Dec. 12, 2006

(65) Prior Publication Data

US 2007/0154919 A1    Jul. 5, 2007

Related U.S. Application Data

(63) Continuation of application No. 10/348,081, filed on Jan. 21, 2003, now Pat. No. 7,227,006.

(60) Provisional application No. 60/360,606, filed on Mar. 1, 2002.

(30) Foreign Application Priority Data

Jan. 19, 2002    (EP)    .................................. 02001401

(51) Int. Cl.
  *C12Q 1/68*    (2006.01)
  *C12Q 1/48*    (2006.01)
  *C12N 15/54*    (2006.01)
(52) U.S. Cl. ............................... 435/6; 435/194; 435/15
(58) Field of Classification Search ........................ None
See application file for complete search history.

(56) References Cited

U.S. PATENT DOCUMENTS 6,143,540 A    11/2000    Kapeller

FOREIGN PATENT DOCUMENTS

EP    0 911 391    4/1999
WO    WO 02/093173    11/2002

OTHER PUBLICATIONS

Feldman Jonathan D. et al., KID-1, A Protein Kinase Induced By Depolarization In Brain, The Journal Of Biological Chemistry, (1998), vol. 273, No. 26, pp. 16535-16543.
Konietzko Uwe et al., Pim Kinase Expression Is Induced By LTP Stimulation And Required For The Consolidation Of Enduring LTP, The EMBO Journal, (1999), vol. 18, No. 12, pp. 3359-3369.
Nadler Samuel T. et al., The Expression Of Adipogenic Genes Is Decreased In Obesity And Diabetes Mellitus, PNAS, (2000), vol. 97, No. 21, pp. 11371-11376.
Mus Musculus, Serine Theronine Kinase pmi3, Clone MGC, Database EMBL Online, (2001), Accession No. BC017621.
Protein Kinase Gene KID-1, Database EMBL Online, (2002), Accession No. BCO26639.
Serine Threonine Kinase (Protein Kinase KID-1), Database EMBL Online, (1998), Accession No. 070444.

*Primary Examiner*—Rebecca Prouty

(57) ABSTRACT

The invention relates to isolated nucleic acid molecules and to host cells comprising such nucleic acid molecules. Moreover, the invention relates to a polypeptide having PIM-3 activity and having a definite amino acid sequence, as well as to the use of PIM-3 as a screening agent for identifying anti-type 2 diabetes mellitus drugs and for preparing a medicament for the treatment of insulin resistance or type 2 diabetes mellitus.

2 Claims, No Drawings

PIM-3 KINASE AS A TARGET FOR TYPE 2 DIABETES MELLITUS

This application is a continuation of U.S. Non-provisional application Ser. No. 10/348,081, filed Jan. 21, 2003, now U.S. Pat. No. 7,227,006, which claims priority under 35 U.S.C. 119 from European Patent Application No. 02001401.5 filed Jan. 19, 2002 and U.S. Provisional Application No. 60/360,606 filed Mar. 1, 2002, both of which are hereby incorporated by reference in their entirety.

FIELD OF THE INVENTION

The present invention relates to a novel use of PIM-3 kinase, to novel PIM-3 kinase subtypes and the use thereof.

BACKGROUND OF THE INVENTION

The rat PIM-3 (originally termed KID-1, KID "kinase induced by depolarisation"), frog PIM-1, and human and murine PIM-1 are all known to have serine/threonine protein kinase activity in in vitro phosphorylation assays. The high polypeptide sequence similarity between human, murine and rat PIM-3, frog PIM-1, and human and murine PIM-1, demonstrates that human and murine PIM-3 are a serine/threonine protein kinase.

Rat PIM-3 is described by Feldman, J. D. et al. (J. Biol. Chem. (1998) 273, 16535 -16543). Rat PIM-3 is induced in specific regions of the hippocampus and cortex in response to kainic acid and electroconvulsive shock suggesting that PIM-3 is involved in neuronal function, synaptic plasticity, learning, and memory as well as kainic acid seizures and some nervous system-related diseases such as seizures and epilepsy.

U.S. Pat. No. 6,143,540, Konietzko, U. et al. (EMBO (1999) 18, 3359-3369) and Eichmann, A. (Oncogene (2000) 19, 1215-1224) also refer to PIM-3 kinase.

SUMMARY OF THE INVENTION

The present invention provides novel PIM-3 encoding sequences and novel uses of PIM-3.

The present invention provides a novel human and murine PIM-3 sequence. SEQ ID NO. 1 depicts the DNA sequence and SEQ ID NO. 2 the predicted amino acid sequence of human PIM-3. The open reading frame of SEQ ID NO:1 extends from nucleotide 17 to nucleotide 995 (SEQ ID NO. 3).

SEQ ID NO. 5 depicts the DNA sequence and SEQ ID NO. 6 the predicted amino acid sequence of murine PIM-3. The open reading frame of SEQ ID NO. 5 extends from nucleotide 199 to nucleotide 1177 (SEQ ID NO. 7).

The present invention demonstrates that expression of the rat PIM-3 gene is decreased in adipocytes in two independent models of insulin resistance. Treatment with an insulin sensitizer causes an increase in PIM-3 gene expression in murine 3T3-L1 cells. Because human and murine PIM-3 is the species ortholog of rat PIM-3, human and murine PIM-3 is involved in some or all of the processes and diseases in which rat PIM-3 is involved. PIM-3, in particular human and murine PIM-3 is involved in development of insulin resistance. In addition PIM-3, in particular human and murine PIM-3 is involved in development of type 2 diabetes mellitus. In addition, the human and murine PIM-3 paralogs, the PIM-1 proteins, are proto-oncogenes. Consequently, PIM-3, in particular human and murine PIM-3 are involved in cell growth regulation, cancer, and related pathways and diseases.

The present invention relates to the use of PIM-3 encoding nucleic acid molecules, PIM-3 proteins and protein homologs in a) screening assays for identifying compounds that modulate insulin resistance or type 2 diabetes mellitus; b) detection assays for detecting insulin resistance or type 2 diabetes mellitus (e.g. chromosomal mapping, tissue typing, forensic biology); c) predictive medicine (prediction of insulin resistance or type 2 diabetes mellitus by e.g. diagnostic assays, prognostic assays, monitoring clinical trials, and pharmacogenomics).

The present invention relates in particular to an isolated nucleic acid molecule comprising nucleotide sequence SEQ ID. NO. 1. The present invention further relates to an isolated nucleic acid molecule comprising nucleotide sequence SEQ ID NO. 3.

The present invention relates to an isolated nucleic acid molecule comprising a nucleotide sequence selected from
 a) SEQ ID NO. 5,
 b) SEQ ID NO. 7,
 c) a DNA sequence which hybridize to SEQ ID NO. 5 or SEQ ID NO. 7, and
 d) DNA sequences which are degenerated as a result of the genetic code to sequences defined in a), b) and c) and which encode for a polypeptide of the PIM-3 type.

The present invention furthermore relates to vectors and host cells comprising the respective DNA sequences or parts thereof.

The present invention relates to polypeptides having PIM-3 activity, said polypeptides being selected from
 a) a polypeptide having amino acid sequence SEQ ID NO. 6,
 b) a polypeptide that in respect to a) is deficient in one or more amino acids,
 c) a polypeptide in which in respect to a) one or more amino acids are replaced with different amino acids,
 d) a polypeptide in which in respect to a) one or more amino acids are added to the sequence,
 e) a fusion polypeptide comprising an amino acid sequence comprising all or a part of the amino acids of sequence SEQ ID NO. 6. Preferably, not more than 10 amino acids are replaced according to c).

The present invention relates to the use of PIM-3 as a screening agent for identifying anti-diabetes mellitus drugs, e.g. the use of PIM-3 encoding DNA or a polypeptide having PIM-3 activity for such purpose.

The present invention further relates to the use of PIM-3 for preparing a medicament for the treatment of insulin resistance or type 2 diabetes mellitus and the use of PIM-3 for predicting insulin resistance or type 2 diabetes mellitus.

DETAILED DESCRIPTION OF THE INVENTION

PIM-3 protein, which interacts with other cellular proteins, can thus be used as a target for developing therapeutic molecules for modulating PIM-3 protein in cells expressing PIM-3 protein or cells involved in the PIM-3 pathway, e.g., adipocytes. Nucleic acid molecules of the invention can be used to express PIM-3 protein (e.g. via a recombinant expression vector in a host cell in gene therapy applications), to detect PIM-3 mRNA (e.g. in a biological sample) or a genetic lesion in a PIM-3 gene, and to modulate PIM-3 activity.

PIM-3 proteins can be used to screen drugs or compounds which modulate the PIM-3 activity or expression as well as to treat disorders characterized by insufficient or excessive production of PIM-3 protein or production of PIM-3 protein forms which have decreased or aberrant activity compared to PIM-3 wild type protein.

The invention provides methods (also referred to herein as a "screening assay") for identifying modulators, i.e. candidate or test compounds or agents (e.g. peptides, peptidomimetics, small molecules or other drugs) which bind to PIM-3 proteins or have a stimulatory or inhibitory effect on, for example, PIM-3 expression or PIM-3 activity.

In one embodiment, the invention provides assays for screening candidate or test compounds which bind to or modulate the activity of a PIM-3 protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection.

In an embodiment, an assay of the present invention is a cell-free assay comprising contacting a PIM-3 protein or biologically active portion thereof with a test compound and determining the ability of the test compound to bind to the PIM-3 protein or biologically active portion thereof. Binding of the test compound to the PIM-3 protein can be determined either directly or indirectly.

In an other embodiment, the assay includes contacting the PIM-3 protein or biologically active portion thereof with a known compound which binds PIM-3 to form an assay mixture, contacting the assay mixture with a test compound, and determining the ability of the test compound to interact with a PIM-3 protein, wherein determining the ability of the test compound to interact with a PIM-3 protein comprises determining the ability of the test compound to preferentially bind to PIM-3 or biologically active portion thereof as compared to the known compound.

In another embodiment, an assay is a cell-free assay comprising contacting PIM-3 protein or biologically active portion thereof with a test compound and determining the ability of the test compound to modulate (e.g., stimulate or inhibit) the activity of the PIM-3 protein or biologically active portion thereof. Determining the ability of the test compound to modulate the activity of PIM-3 can be accomplished, for example, by determining the ability of the PIM-3 protein to bind to a PIM-3 target molecule, this means determining direct binding. In an alternative embodiment, determining the ability of the test compound to modulate the activity of PIM-3 can be accomplished by determining the ability of the PIM-3 protein to further modulate an PIM-3 target molecule. For example, the catalytic/enzymatic activity of the target molecule on an appropriate substrate can be determined.

In another embodiment, the cell-free assay comprises contacting the PIM-3 protein or biologically active portion thereof with a known compound which binds PIM-3 to form an assay mixture, contacting the assay mixture with a test compound, and determining the ability of the test compound to interact with the PIM-3 protein, wherein determining the ability of the test compound to interact with the PIM-3 protein comprises determining the ability of the PIM-3 protein to preferentially bind to or modulate the activity of a PIM-3 target molecule.

Phosphoaminoacid analysis of the phosphorylated substrate can also be performed in order to determine which residues on the PIM-3 substrate are phosphorylated. Briefly, the radiophosphorylated protein band can be excised from the SDS gel and subjected to partial acid hydrolysis, The products can then be separated by one-dimensional electrophoresis and analyzed on, for example, a phosphoimager and compared to ninhydrin-stained phosphoaminoacid standards.

In another embodiment of the invention, the cell free assay determines the ability of the PIM-3 protein to phosphorylate a PIM-3 target molecule by, for example, an in vitro kinase assay. Briefly, a PIM-3 target molecule, e.g., an immunoprecipitated PIM-3 target molecule from a cell line expressing such a molecule, can be incubated with the PIM-3 protein and radioactive ATP.

In another embodiment, an assay is a cell-based assay in which a cell which expresses a soluble form of PIM-3 protein, or a biologically active portion thereof, is contacted with a test compound and the ability of the test compound to bind to a PIM-3 protein determined. The cell, for example, can be a yeast cell or a cell of mammalian origin. Determining the ability of the test compound to bind to the PIM-3 protein can be accomplished, for example, by coupling the test compound with a radioisotope or enzymatic label such that binding of the test compound to the PIM-3 protein or biologically active portion thereof can be determined by detecting the labeled compound in a complex, e.g. with $^{125}$I, $^{35}$S, $^{14}$C, or $^{3}$H, or enzymatically with, for example, horseradish peroxidase, alkaline phosphatase, or luciferase.

In another embodiment, an assay is a cell-based assay comprising contacting a cell expressing a soluble form of PIM-3 protein, or a biologically active portion thereof, with a test compound and determining the ability of the test compound to modulate (e.g., stimulate or inhibit) the activity of the PIM-3 protein or biologically active portion thereof. Determining the ability of the test compound to modulate the activity of PIM-3 or a biologically active portion thereof can be accomplished, for example, by determining the ability of the PIM-3 protein to bind to or interact with an PIM-3 target molecule.

As used herein, a "target molecule" is a molecule with which an PIM-3 protein binds or interacts in nature, for example, a substrate molecule phosphorylated by PIM-3 protein in the interior of a cell which expresses a PIM-3 protein, the intracellular domains of transmembrane receptors, a molecule associated with the internal surface of a cell membrane or a cytoplasmic molecule. A PIM-3 target molecule can be a non-PIM-3 molecule or a PIM-3 protein or polypeptide of the present invention. In one embodiment, a PIM-3 target molecule is a component of a signal transduction pathway, which mediates transduction of a signal.

In an embodiment, determining the ability of the PIM-3 protein to bind to or interact with a PIM-3 target molecule can be accomplished by determining the activity of the target molecule. For example, the activity of the target molecule can be determined by detecting induction of a cellular second messenger of the target (e.g., intracellular $Ca^{2+}$, diacylglycerol, IP3, etc.), detecting catalytic/enzymatic activity of the target on an appropriate substrate, detecting the induction of a reporter gene (e.g., a PIM-3-responsive regulatory element operably linked to a nucleic acid encoding a detectable marker, e.g. luciferase), or detecting a cellular response, for example, cellular differentiation, or cell proliferation.

In various formats of the assay methods of the present invention, it may be desirable to immobilize either PIM-3 or its target molecule to facilitate separation of complexed from uncomplexed forms of one or both of the proteins, as well as to accommodate automation of the assay. Binding of a test compound to PIM-3, or interaction of PIM-3 with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/PIM-3 fusion proteins or glutathione-S-transferase/target fusion proteins can be adsorbed onto glutathione sepharose beads or glutathione derivatized microtitre plates, which are then combined with the test compound or the test compound and either the non-adsorbed target protein or PIM-3 protein, and the mixture incubated under conditions conducive to complex formation (e.g., at physiological conditions for salt and pH). Following incubation, the beads or microtitre plate wells are washed to remove any unbound components and complex formation is measured either directly or indirectly. Alternatively, the complexes can be dissociated from the matrix, and the level of PIM-3 binding or activity determined using standard techniques.

Other techniques for immobilizing proteins on matrices can also be used in the screening assays of the invention. For example, either PIM-3 or its target molecule can be immobilized utilizing conjugation of biotin and streptavidin. Biotinylated PIM-3 or target molecules can be prepared from biotin-NHS (N-hydroxy-succinimide) using techniques well known in the art. Alternatively, antibodies reactive with PIM-3 or target molecules but which do not interfere with binding of the PIM-3 protein to its target molecule can be derivatized to the wells of the plate, and unbound target or PIM-3 trapped in the wells by antibody conjugation. Methods for detecting such complexes, in addition to those described above for the GST-immobilized complexes, include immunodetection of complexes using antibodies reactive with the PIM-3 or target molecule, as well as enzyme-linked assays, which rely on detecting an enzymatic activity associated with the PIM-3 or target molecule.

In another embodiment, modulators of PIM-3 expression are identified in a method in which a cell is contacted with a candidate compound and the expression of PIM-3 mRNA or protein in the cell is determined. The level of expression of PIM-3 mRNIA or protein in the presence of the candidate compound is compared to the level of expression of PIM-3 mRNA or protein in the absence of the candidate compound. The candidate compound can then be identified as a modulator of PIM-3 expression based on this comparison. For example, when expression of PIM-3 mRNA or protein is greater (statistically significantly greater) in the presence of the candidate compound than in its absence, the candidate compound is identified as a stimulator of PIM-3 mRNA or protein expression. Alternatively, when expression of PIM-3 mRNA or protein is less (statistically significantly less) in the presence of the candidate compound than in its absence, the candidate compound is identified as an inhibitor of PIM-3 mRNA or protein expression. The level of PIM-3 mRNA or protein expression in the cells can be determined by methods described herein for detecting PIM-3 mRNA or protein.

In another aspect of the invention, the PIM-3 proteins or polypeptides thereof can be used as "bait proteins" in a two-hybrid assay or three hybrid assay, to identify other proteins, which bind to or interact with PIM-3 ("PIM-3-binding proteins" or "PIM-3-bp") and modulate PIM-3 activity. Such PIM-3-binding proteins are also likely to be involved in the propagation of signals by the PIM-3 proteins as, for example, upstream or downstream elements of the PIM-3 pathway. The invention also provides for the use of proteins that interact with PIM-3, e.g., two-hybrid interactors with PIM-3, as baits in two-hybrid screens and the identification of PIM-3 interacting protein interacting proteins. PIM-3 interacting protein interacting proteins are likely to be involved in the PIM-3 signal transduction pathway.

The present invention also provides the field of predictive medicine in which diagnostic assays, prognostic assays, pharmacogenomics, and monitoring clinical trials are used for prognostic (predictive) purposes to thereby treat an individual prophylactically. Accordingly, one aspect of the present invention relates to diagnostic assays for determining PIM-3 protein and/or nucleic acid expression as well as PIM-3 activity, in the context of a biological sample (e.g., blood, serum, cells, tissue form the individual, preferably human) to thereby determine whether an individual is afflicted with a disease or disorder, or is at risk of developing a disorder, associated with aberrant PIM-3 expression or activity. The invention also provides for prognostic (or predictive) assays for determining whether an individual is at risk of developing a disorder associated with PIM-3 protein, nucleic acid expression or activity. For example, mutations in a PIM-3 gene can be assayed in a biological sample. Such assays can be used for prognostic or predictive purpose to thereby prophylactically treat an individual prior to the onset of a disorder characterized by or associated with PIM-3 protein, nucleic acid expression or activity.

Another aspect of the invention provides methods for determining PIM-3 protein, nucleic acid expression or PIM-3 activity in an individuals biological sample to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Another aspect of the invention provides monitoring the influence of agents (e.g., drugs or other compounds) on the expression or activity of PIM-3 in clinical trials.

An exemplary method for detecting the presence or absence of PIM-3 in a biological sample involves obtaining a biological sample from a test subject and contacting the biological sample with a compound or an agent capable of is detecting PIM-3 protein or nucleic acid (e.g., mRNA, genomic DNA) that encodes PIM-3 protein such that the presence of PIM-3 is detected in the biological sample. An agent for detecting PIM-3 mRNA or genomic DNA can be a labeled nucleic acid probe capable of hybridizing to PIM-3 mRNA or genomic DNA.

An agent for detecting PIM-3 protein can be an antibody capable of binding to PIM-3 protein, preferably an antibody with a detectable label. Antibodies can be polyclonial, or more preferably, monoclonal. An intact antibody, or a fragment thereof (e.g., Fab or F(ab').sub.2) can be used.

The term "biological sample" is intended to include tissues, cells and biological fluids isolated from an individual, as well as tissues, cells and fluids present within an individual. That is, the detection method of the invention can be used to detect PIM-3 mRNA, protein, or genomic DNA in a biological sample e.g. in vitro as well as or in vivo. In one embodiment, the biological sample contains protein molecules from the test subject. Alternatively, the biological sample can contain mRNA molecules from the test subject or genomic DNA molecules from the test subject. A biological sample is e.g. a biopsy from adipose tissue isolated by conventional means from a subject.

In another embodiment, the methods further involve obtaining a control biological sample from a control subject, contacting the control sample with a compound or agent capable of detecting PIM-3 protein, mRNA, or genomic DNA, such that the presence of PIM-3 protein, mRNA or genomic DNA is detected in the biological sample, and comparing the presence of PIM-3 protein, mRNA or genomic DNA in the control sample with the presence of PIM-3 protein, mRNA or genomic DNA in the test sample.

The invention also encompasses kits for detecting the presence of PIM-3 in a biological sample (a test sample). Such kits can be used to determine if an individual is suffering from or is at increased risk of developing a disorder associated with insulin resistance or type 2 diabetes. For example, the kit can comprise a labeled compound or agent capable of detecting PIM-3 protein or mRNA in a biological sample and means for determining the amount of PIM-3 in the sample (e.g., an anti-PIM-3 antibody or an oligonucleotide probe which binds to DNA encoding PIM-3, e.g., SEQ ID NO:1, SEQ ID NO:3, SEQ ID NO. 5 or SEQ ID NO. 7).

The methods described herein can furthermore be utilized as diagnostic or prognostic assays to identify subjects having or at risk of developing a disease or disorder associated with aberrant PIM-3 expression or activity. For example, the assays described herein, such as the preceding diagnostic assays or the following assays, can be utilized to identify a subject having or at risk of developing insulin resistance or type 2 diabetes. Thus, the present invention provides a method in which PIM-3 protein or nucleic acid (e.g., mRNA, genomic DNA) is detected in a test sample from an individual, wherein the presence of PIM-3 protein or nucleic acid is diagnostic for the individual for having or at risk of developing a disease or disorder associated with aberrant PIM-3 expression or activity. As used herein, a "test sample" refers to a biological sample obtained from a subject of interest. For example, a test sample can be a biological fluid (e.g., serum), cell sample, or tissue.

Furthermore, the prognostic assays can be used to determine whether a subject can be administered an agent (e.g., an agonist, antagonist, peptidomimetic, protein, peptide, nucleic acid, small molecule, or other drug candidate) to treat insulin resistance or type 2 diabetes. For example, such methods can be used to determine whether a subject can be effectively treated with a specific agent or class of agents (e.g., agents of a type which decrease PIM-3 activity).

Agents, or modulators which have a stimulatory or inhibitory effect on PIM-3 activity (e.g., PIM-3 gene expression) as identified by a screening assay can be used for preparing a pharmaceutical which is useful for treating (prophylactically or therapeutically) disorders (e.g., disorders involving cells or tissues in which PIM-3 is expressed, such as adipocytes) associated with aberrant PIM-3 activity. In conjunction with such treatment, the pharmacogenomics (i.e. the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of PIM-3 protein, expression of PIM-3 nucleic acid, or mutation content of PIM-3 genes in an individual can be determined to thereby select appropriate agent(s) for therapeutic or prophylactic treatment of the individual.

Monitoring the influence of agents (e.g., drugs, compounds) on the expression or activity of PIM-3 (e.g., the ability to modulate aberrant cell proliferation and/or differentiation) can be applied not only in basic drug screening, but also in clinical trials.

An anti type 2 diabetes agent that modulates PIM-3 protein activity can be an agent, such as a small molecule, e.g., a small molecule that modulates the protein kinase activity of PIM-3, a nucleic acid or a protein, a naturally-occurring cognate ligand of a PIM-3 protein, a peptide, or a PIM-3 peptidomimetic. In one embodiment, the agent stimulates one or more of the biological activities of PIM-3 protein. Examples of such stimulatory agents include small molecules that stimulate one or more activities of PIM-3, e.g., the PIM-3 protein kinase activity, active PIM-3 protein and a nucleic acid molecule encoding PIM-3 that has been introduced into the cell. In another embodiment, the agent inhibits one or more of the biological activities of PIM-3 protein. Examples of such inhibitory agents include a small molecule that inhibits one or more PIM-3 activities e.g., PIM-3 protein kinase activity, antisense PIM-3 nucleic acid molecules and anti-PIM-3 antibodies.

This invention is further illustrated by the following examples which should not be construed as limiting. The contents of all references, patents and published patent applications cited throughout this application are hereby incorporated by reference.

EXAMPLES

Example 1

Determination of the Nucleotide Sequence of Human and Murine PIM-3

Rat PIM-3 nucleotide sequence (AF057026, NM_022602, SEQUENCE ID NO:9) was used to query a proprietary database using the BLASTN program with the BLOSUM62 matrix, This proprietary database is based on a proprietary cDNA library, which is constructed in standard cloning vectors. The most closely related cDNA clones identified by this BLASTN were sequenced. The cDNA sequences were assembled into a contig. The human PIM-3 sequence was determined from the consensus sequence of this contig, further analysis of this contig revealed a cDNA sequence 1977 bp in length. That human PIM-3 cDNA contains a 978 base pair open reading frame predicted to encode a novel 326 amino acid protein.

Rat PIM-3 nucleotide sequence was also used to query the public UNIGENE Mouse database using the BLASTN program with the BLOSUM62 matrix. Some closely related EST sequences were identified by this BLASTN. Sequence information of this ESTs was used to screen a mouse embryo cDNA library constructed using the Gene Trapper II Technology (Life Technologies, Karlsruhe, Germany). A cDNA clone was sequenced, and the cDNA sequences were assembled into a contig. The murine PIM-3 sequence was determined from the consensus sequence of this contig, further analysis of this contig and exclusion of an intron sequence revealed a cDNA sequence 2236 bp in length. That murine PIM-3 cDNA contains a 978 base pair open reading frame predicted to encode a novel 326 amino acid protein.

Example 2

Characterization of the Human and the Murine PIM-3 Protein

In this example, the predicted amino acid sequence of human PIM-3 and the murine PIM-3 protein was compared to amino acid sequences of known motifs and/or domains present in proteins and to the polypeptide sequences of known proteins. Polypeptide domains and/or motifs present in human PIM-3 and murine PIM-3 were identified as were proteins with significant amino acid similarities to human PIM-3 and murine PIM-3. In addition, the molecular weight of the human PIM-3 and the murine PIM-3 protein was predicted.

The human and the murine nucleotide sequences (SEQ ID NO. 1; SEQ ID NO.5), identified as described above, encode a 326 amino acid protein (SEQ ID NO.2 and SEQ ID NO. 6). Human and murine PIM-3 has a predicted MW of about 35.9 kDa, respectively, not including post-translational modifications. To check for evidences for a putative kinase activity and for possible posttranslational modification sites, the human and the murine polypeptde sequences of SEQ ID NO. 2 and SEQ ID NO. 6, respectively, were analyzed using the PROSITE database of protein patterns, as well as using IMPALA and PFAM.

Searching the PROSITE database revealed the presence of one cAMP and cGMP dependent protein kinase phosphorylation site from amino acids 260-263 of SEQ ID NO.2 and SEQ ID NO.6; three Casein kinase II phosphorylation sites from amino acids 202-205, 211-214 and 321-324 of SEQ ID NO.2 and four Casein kinase II phosphorylation sites from amino acids 202-205, 211-214 299-302 and 321-324 of SEQ ID NO.6; ten N-myristoylation sites from amino acids 43-48, 49-54, 52-57, 57-62, 63-68, 80-85, 98-103, 101-106, 295-300 and 316-321 of SEQ ID NO. 2 and SEQ ID NO.6; three Protein kinase C phosphorylation sites from amino acids 137-139, 275-277 and 279-281 of SEQ ID NO.2 and SEQ ID NO.6; one tyrosine kinase phosphorylation site from amino acids 33-40 of SEQ ID NO.2 and SEQ ID NO.6; one protein kinase signature and profile (ATP binding site) from amino acids 46-69 of SEQ ID NO.2 and SEQ ID NO.6; one serine/threonine protein kinase active site signature from amino acids 166-178 of SEQ ID NO.2 and SEQ ID NO.6. The search using IMPALA revealed the presence of one eukaryotic protein kinase domain from amino acid 40-293 (SEQ ID NO.4 and SEQ ID NO.8, respectively), of SEQ ID NO.2 and SEQ ID NO. 6; with a score of 186 bits and Expect value of 8e-49 and with a score of 184 bits and Expect value of 4e-48, respectively. The search using PFAM revealed also the presence of one eukaryotic protein kinase domain from amino acid 40-293, of SEQ ID NO. 2 and SEQ ID NO. 6; with a score of 262,5 and E-value of 5.7e-75 and with a score of 261,1 bits and E-value of 1.5e-74, respectively.

The human, murine and rat PIM-3 polypeptide sequences (SEQ ID NO.2, SEQ ID NO.6 and SEQ ID NO.10) were aligned in a pair wise Clustal W alignment analysis using blosum as the protein weight matrix. Thereby, human PIM-3 was found to be 95% identical to murine and rat PIM-3 (AF057026, NM_022602, SEQ ID NO.10) with a score of 2011, murine PIM-3 was found to be 99% identical to rat PIM-3 (AF057026, NM_022602, SEQ ID NO.10) with a score of 2074.

The human and the murine PIM-3 polypeptide sequences of SEQ ID NO.2 and of SEQ ID NO. 6 was also used to query the Swissprot database of protein sequences using the BLASTP program with the BLOSUM62 matrix. The four most closely related proteins to human and murine PIM-3 identified by this BLASTP analysis are listed: Human and murine PIM-3 was found to be 76% identical to *Xenopus laevis* (frog) PIM-1 (Q91822; SEQ ID NO. 11) with a score of 518, 72% identical to rat PIM-1 (P26794; SEQ ID NO. 12) with a score of 442, 71% identical to human PIM-1 (P11309; SEQ ID NO. 13) with a score of 441 and 71% identical to murine PIM-1 (P06803; SEQ ID NO. 14) with a score of 436 and 438, respectively.

Example 3

Gene Expression of PIM-3 in an in Vivo Model of Insulin Resistance and Type 2 Diabetes Mellitus Zucker diabetic fatty (ZDF) rats are well known animal model carrying a homozygous defect in the leptin receptor fa gene. This rat strain develops age dependent an insulin resistant/hyperinsulinaemic state which than progresses to overt type 2 diabetes mellitus/hyperglycaemic state. To identify genes the expression of which is either induced or repressed and so may contribute or mark the development of insulin resistance or type 2 diabetes mellitus, gene expression profiles of ZDF rats and their lean heterozygous control littermates were collected using oligonucleotide array based profiling technique.

Material and Methods:

Zucker Diabetic Fatty (ZDF/Gmi.TM.–fa/fa) male rats as well as their lean male fa+/fa– counterparts, used as healthy controls, aged 6, 8 and 13 weeks were obtained from Genetic Models Inc. (Indianapolis, Ind., US).

Before the animals were included into the study they were kept under standard animal house conditions for one week. For collection of epididymal fat tissue and blood samples the animals were killed by cervical dislocation. 6 ZDF rats and 6 lean fa+/fa–littermates per age group were used for gene expression analysis as described below.

Tissue Collection and RNA Isolation:

Following cervical dislocation, epididymal fat pads were surgically removed, portioned and quickly transferred in suitable tubes containing sufficient volumes of RNA later (Ambion, Tex., US). Samples from each animal were stored individually. Long term storage of the samples was performed at minus 80.degree.C.

Total cellular RNA was extracted from adipose tissue using Rneasy Mini kit (Qiagen, Hilden, Germany) according to the manufacturers recommendations for RNA isolation from fat tissue. RNA was eluted twice in 50. mul RNAse free water, RNA concentration was determined spectroscopically (A.sub.260).

For further purification, RNA solution was filled up to 100 µl total volume with RNase free water. RNA clean up was performed according to the manufacturers instructions using Qiagein Rneasy Mini kit. RNA was eluted twice in 50 µl RNase free water, RNA concentration was determined spectroscopically (A.sub.260).

For concentration of the RNA eluate, NH.sub.4 acetate and ethanol were added, and RNA was precipitated overnight in an ethanol-dry ice bath. RNA was collected by centrifugation at maximum speed at 4.degree.C. Pelleted RNA was washed twice with 80% ethanol, air dried and dissolved in a small volume of RNAse free water. Rnase concentration was determined spectroscopically (A.sub.260).

Gene Expression Profiling:

The general use of oligonucleotides arrays for gene expression monitoring has been described in U.S. Pat. No. 6,177,248. In our practical application, the used microarrays contain desoxynucleotide sequences that represent approximately 8000 known genes or EST clusters. Each gene or EST sequence is represented by up to 20 pairs of oligonucleoitides, each pair consisting of one oligo that matches to a segment of the transcript, and a control oligo that contains a centrally located 1 bp mismatch. For rat, 3 arrays (RG U34A, RG U34B and RG U34C) representing approximately 24000 gene and EST sequences in total, derived from a database of known genes or EST sequences are provided by Affymetrix, Santa Clara, Calif., US.

cRNA Preparation for Hybridization:

RNA was obtained from epididymal fat as decribed above. An oligo dT primer containing al T7 promotor site was added to total cellular RNA (10.mu.g)+–. After annealing of the primer, the RNA was subsequently reverse transcribed using Superscript choice reverse transcriptase, following the manufacturers instructions. After extraction with phenol:chloroform:isoamylalcohol, using phase lock gel tubes (Eppendorf, Hamburg, Germany), and ethanol precipitation, the cDNA was collected by centrifugation and washed twice with 80% ethanol. The pellet was dissolved in Rnase free water and transcribed into biotinylated cRNA using the Enzo HighYield labeling transcription kit (Enzo Diagnostics, Farmingdale N.Y., US) or MEGAscript T7 high yield transcription kit (Ambion, Austin, Tex., US) according the manufacturers instructions. For the latter application, biotin labeled UTP and CTP (Sigma, Munich, Germany) plus unlabelled ATP and GTP was used in a molar ratio of 1:3 (labeled vs unlabeled). cRNA was then precipitated and washed as described above. Finally, the precipitated, air dried cRNA was dissolved in a small volume of RNAse free water. RNA concentration was determined spectroscopically ($A_{260}$), and size distribution was checked by agarose gelelectrophoresis. Subsequently, CRNA was hydrolized to an average size of 50 nucleotides in length by incubating for 25 minutes in 40 mM Tris-acetate pH 8.1, 100 mM potassium acetate, 30 mM magnesium acetate at 94.degree.C. 20. µg of the fragmented cRNA was used to set up of a hybridisation cocktail according to the instructions of Affymetrix. Prior hybridization, RNA samples were heated in the hybridization cocktails to 99.degree.C. for 10 min, placed on ice for 5 min, and allowed to equilibrate to room temperature before being placed in the hybridization flow cell. The hybridization cocktail was then hybridized to a microarray at 45° C. and 60 rpm in a hybridization oven overnight. After hybridization, the hybridization cocktail was removed and stored at minus 80° C.) for further use. The arrays were washed and stained in a Affymetrix fluidics station using the phycoerythrin -steptavidin -antibody amplification protocol EukWS2 according to the manufacturers instructions. Data were collected using a scanning confocal microscope made for Affymetrix by Hewlett Packard (Commercially available through Affymetrix, Santa Clara, Calif., US.). The scanner uses an argon ion laser as the excitation source, with the emission detected by a photomultiplier tube through either a 530 nm bandpass filter (fluorescein) or a 560 nm longpass filter (phycoerythrin).

Quantitative Analysis of Hybridization Patterns and Intensities:

Following a quantitative scan of an array, a grid is aligned to the image using the known dimensions of the array and the corner control regions as markers. The image is reduced to a simple text file containing position and intensity information using software developed at Affymetrix (available with the confocal scanner). This information is merged with another text file that contains information relating physical position on the array to probe sequence and the identity of the RNA (and the specific part of the RNA) for which the oligonucleotide probe is designed. The quantitative analysis of the hybridization results involves a simple form of pattern recognition based on the assumption that, in the presence of a specific RNA, the PM (PM means "perfect match" in U.S. Pat. No. 6,177,248) probes will hybridize more strongly on average than their MM (MM means "mismatch" in U.S. Pat. No. 6,177,248) partners. The number of instances in which the PM hybridization signal is larger than the MM signal is computed along with average of the logarithm of the PM/MM ratios for each probe set. These values are used to make a decision (using a predefined decision matrix) concerning the presence or absence of an RNA. To determine the quantitative RNA abundance, the average of the differences (PM minus MM) for each probe family is calculated. The advantage of the difference method is that signals from random cross-hybridization contribute equally, on average, to the PM and MM probes, while specific hybridization contributes more to the PM probes. By averaging the pairwise differences, the real signals add constructively while the contributions form cross-hybridization tend to cancel. When assessing the differences between two different RNA samples, the hybridization signals from side-by-side experiments on identically synthesized arrays are compared directly. The magnitude of the changes in the average of the difference (PM-MM) values is interpreted by comparison with the results of spiking experiments as well as the signals observed for the internal standard bacterial and phage RNAs spiked into each sample at a known amount. Data analysis programs developed at Affymetrix perform these operations automatically.

TABLE 1

| | ZDF rats, 7 weeks old | | | | |
|---|---|---|---|---|---|
| Comparison | ZDF #1 vs control #1 | ZDF #2 vs control #2 | ZDF #3 vs control #3 | ZDF #4 vs control #4 | ZDF #5 vs control #5 |
| Fold change | −4.3 | −4.8 | −3.1 | −5.3 | −4.6 |

TABLE 2

| | ZDF rats, 9 weeks old | | | | |
|---|---|---|---|---|---|
| Comparison | ZDF 7 vs control #7 | ZDF 8 vs control #8 | ZDF 9 vs control #9 | ZDF 10 vs control #10 | ZDF 11 vs control #11 |
| Fold change | −5.4 | −3.3 | −2.9 | −1.7 | −1.3 |

TABLE 3

| | ZDF rats, 14 weeks old | | | | |
|---|---|---|---|---|---|
| Comparison | ZDF 13 vs control #13 | ZDF 14 vs control #14 | ZDF 15 vs control #15 | ZDF 16 vs control #16 | ZDF 17 vs control #17 |
| Fold Change | 1 | −1.7 | −3.0 | −2.4 | −1.7 |

Example 4

Gene Expression of PIM-3 in an In vitro Model of Insulin Resistance

Adipocytes were isolated from epididymal fat pads of 160-180 g male Sprague Dawley rats and incubated as described (Müller, G. and Wied, S., Diabetes (1993) 42: 1852-1867). Briefly, adipocytes were isolated from the pooled epididymal fat of 20 male rats. The isolated adipocytes were split into two pools. One pool was made insulin resistant by incubating the cells for 5 hours in medium containing 25 mM D-glucose plus 10 nM insulin.

The second pool was incubated for 5 h in medium containing 5 mM D-glucose, which kept the cells in the insulin sensitive state. At the end of the incubation insulin sensitivity and insulin resistance where checked by measuring insulin dependent glucose uptake with an aliquot of the two pools as described (Müller, G. and Wied, S. Diabetes (1993) 42: 1852-1867). The majority of the adipocytes was used for isolating RNA as described in example 3.

Subsequently RNA was used for gene expression monitoring using Affymetrix technology as described in example 3. Fold changes of gene expression for PIM-3 were analyzed using the Affimetrix qualifier AF086624_S_AT. The results of these analysis are summarized in table 4:

TABLE 4

| | In vitro insulin resistant adipocytes, 5 h incubated | | | | |
|---|---|---|---|---|---|
| Comparison | Resistant 1 vs control 1 | Resistant 2 vs control 2 | Resistant 3 vs control 3 | Resistant 4 vs control 4 | Resistant 5 vs control 5 |
| Fold change | −2.4 | −2.7 | −4.0 | −2.1 | −2.4 |

TABLE 5

| probe no. | compound* | concentration | duration of treatment |
|---|---|---|---|
| 1 | rosiglitazone | 1 µM | 6 hours |
| 2 | rosiglitazone | 5 µM | 6 hours |
| 3 | troglitazone | 1 µM | 6 hours |
| 4 | troglitazone | 5 µM | 6 hours |
| 5 | DMSO control | 0.02% (v/v) | 6 hours |
| 6 | rosiglitazone | 1 µM | 24 hours |
| 7 | rosiglitazone | 5 µM | 24 hours |
| 8 | troglitazone | 1 µM | 24 hours |
| 9 | troglitazone | 5 µM | 24 hours |
| 10 | DMSO control | 0.02% (v/v) | 24 hours |
| 11 | rosiglitazone | 1 µM | 48 hours |
| 12 | rosiglitazone | 5 µM | 48 hours |
| 13 | troglitazone | 1 µM | 48 hours |
| 14 | troglitazone | 5 µM | 48 hours |
| 15 | DMSO control | 0.02% (v/v) | 48 hours |

*5 mM and 25 mM stock solutions of rosiglitazone and troglitazone dissolved in DMSO were made and diluted 5000fold to the final concentrations (1 µM/5 µM) in the culture medium. For the controls, DMSO without compound was equally diluted 5000fold to a final concentration of 0.02% (v/v).

RNA was isolated using the TRIzol reagent (Life Technologies, Karlsruhe, Germany) and treated with DNase I by applying the DNA-free kit (Ambion, Austin, Tex., US).

Experiments 5

Gene Expression of PIM-3 in 3T3-L1 Adipocytes Treated with Antidiabetic Drugs (PPARγ Agonists)

Material and Methods:

3T3-L1 preadipocytes were grown at 37° C. in 10% $CO_2$ in Dulbecco's modified Eagle's medium (DMEM) containing 1 g/l glucose and 10% fetal calf serum (FCS). For differentiation into mature adipocytes, confluent preadipocytes were cultured for four days in DMEM supplemented with 4.5 g/l glucose, 10% FCS, 50 µg/ml ascorbic acid, 1 µM biotin, 17 µM pantothenic acid (=basal medium), 500 µM 3-isobutylmethylxanthine, 0.25 µM dexamethasone and 1 µg/ml human recombinant insulin. During the four day treatment the medium was changed once. Finally, 3T3-L1 cells were treated for three days with basal medium containing 1 µg/ml insulin whereupon approximately 90% of the cells were converted into adipocytes.

Differentiated 3T3-L1 cells were maintained in basal medium for one additional day and subsequently kept in serum-free basal medium for four hours. Then, PPARγ agonists diluted in basal medium were added to the adipocytes as described below centrations and conditions see table 5):

Further purification of the RNA was achieved using the RNeasy mini kit (Qiagen, Hilden, Germany) and quality/quantity control was done with the 2100Bioanalyzer (Agilent, Böblingen, Germany). 10 µg of total RNA was converted into biotinylated cRNA according to the GeneChip expression analysis technical manual (Affymetrix, Santa Clara, Calif., US). Briefly, first and second strand synthesis was performed by applying the SuperScript double stranded cDNA synthesis kit (Life Technologies, Kardsruhe, Germany) and biotin labeled cRNA was produced with the Bio-Array RNA transcript labeling kit (Enzo Diagnostics, Framingdale, N.Y., US). 10 µg of cRNA was fragmented by heat, added to the GeneChip eukaryotic hybridization control solution (Affymetrix) and hybridized to a GeneChip MG-U74Av2 array (Affymetrix) by rotating for 16 hours at 45° C. Washing, staining and scanning of the array was carried outwith standard procedures using the hardware provided by Affymetrix. Raw data was analyzed by applying the microarray suite version 4.0.1 software (Affymetrix, see above).

The entire experiment was repeated twice to provide three biological replicates.

Data Analysis:

Data analysis including the estimation of fold changes was performed as described above. Fold change values for PIM-3 were obtained by comparing the compound treated samples against the untreated controls for each time point. Therefore, Affymetrix qualifier 96841_AT was used.

The results, are summarized in table 6a)-c).

TABLE 6a

|  | 6 hours | | | | 24 hours | | | | 48 hours | | | |
| --- | --- | --- | --- | --- | --- | --- | --- | --- | --- | --- | --- | --- |
|  | Rosi 1 µM | Rosi 5 µM | Tro 1 µM | Tro 5 µM | Rosi 1 µM | Rosi 5 µM | Tro 1 µM | Tro 5 µM | Rosi 1 µM | Rosi 5 µM | Tro 1 µM | Tro 5 µM |
| comparison | 1/5 | 2/5 | 3/5 | 4/5 | 6/10 | 7/10 | 8/10 | 9/10 | 11/15 | 12/15 | 13/15 | 14/15 |
| Fold change | 2.1 | 2.2 | 1.7 | 2.1 | 2.9 | 2.9 | 1.8 | 2.7 | 2.6 | 2.6 | 1.8 | 2.4 |

TABLE b

|  | 6 hours | | | | 24 hours | | | | 48 hours | | | |
| --- | --- | --- | --- | --- | --- | --- | --- | --- | --- | --- | --- | --- |
|  | Rosi 1 µM | Rosi 5 µM | Tro 1 µM | Tro 5 µM | Rosi 1 µM | Rosi 5 µM | Tro 1 µM | Tro 5 µM | Rosi 1 µM | Rosi 5 µM | Tro 1 µM | Tro 5 µM |
| comparison | 1/5 | 2/5 | 3/5 | 4/5 | 6/10 | 7/10 | 8/10 | 9/10 | 11/15 | 12/15 | 13/15 | 14/15 |
| Fold change | 1.5 | 1.3 | 1.7 | 1.7 | 2.2 | 1.9 | 1.6 | 1.9 | 2.0 | 1.9 | 1.6 | 1.9 |

TABLE c

|  | 6 hours | | | | 24 hours | | | | 48 hours | | | |
| --- | --- | --- | --- | --- | --- | --- | --- | --- | --- | --- | --- | --- |
|  | Rosi 1 µM | Rosi 5 µM | Tro 1 µM | Tro 5 µM | Rosi 1 µM | Rosi 5 µM | Tro 1 µM | Tro 5 µM | Rosi 1 µM | Rosi 5 µM | Tro 1 µM | Tro 5 µM |
| comparison | 1/5 | 2/5 | 3/5 | 4/5 | 6/10 | 7/10 | 8/10 | 9/10 | 11/15 | 12/15 | 13/15 | 14/15 |
| Fold change | 2.0 | 2.2 | 1.8 | 2.3 | 1.9 | 1.3 | 1.6 | 2.0 | 2.1 | 2.0 | 1.6 | 2.3 |

"Rosi" stands for "rosiglitazone", "Tro" stands for "troglitazone".

Example 6

Gene Expression of Pim-3 in ZDF Rats Treated with Anti-diabetic Drugs (PPARγ Agonists)

Zucker Diabetic Fatty (ZDF/Gmi.TM.–fa/fa) male rats as well as their lean fa+/fa– counterparts, aged 5 weeks (control 1-5, ZDF 1-10)were obtained from Genetic Models Inc. (Indianapolis, Ind.). The rats were given free access to food and water. The ZDF animals were split into 2 groups: group 1(animals ZDF 1-5) was not treated with any agent, whereas the second group was treated for 14 weeks with the antidiabetic drug Rosiglitazone (3 mg/kg/day, animals 6-10, Rosi 1-5,). For the collection of epididymal fat pads and also blood samples, in each case 5 animals were sacrificed by cervical dislocation. To monitor the success of the antidiabetic treatment, HbA1c as marker of long-term blood glucose levels were measured by standard methods after finishing of the experiment. The results of these measurements are summarized in table 7:

Collection of epididymal adipose tissue, RNA isolation and Affymetrix experiments were performed as described in experiment 1. Data analysis included the comparison of expression data of samples derived from the lean control animals versus the untreated ZDF rats as well as the comparison of the expression data derived from Rosiglitazone treated ZDF animals versus non-treated ZDF animals. Data analysis including the estimation of fold changes and weighing of the statistical significance of those fold changes was performed using a proprietary software developed in Aventis pharmaceuticals. Fold changes of gene expression for Pim-3 were analyzed using the Affymetlrix qualifier AF086624_S_AT. The results of those analysis are summarized in the following tables 8a und 8b:

TABLE 8a

|  | ZDF rats, 20 weeks old | | | | |
| --- | --- | --- | --- | --- | --- |
| comparison | ZDF 1 vs control #1 | ZDF 2 vs control #2 | ZDF 3 vs control #3 | ZDF 4 vs control #4 | ZDF 5 vs control #5 |
| Fold change | −1.5 | −1.8 | −1.6 | 1 | −1.7 |

TABLE 7

% HbA1c in different rats: control (x) rats (C), ZDP rats untreated (Z), ZDF rats Rosiglitazone treated (R)

| animal | C1 | C2 | C3 | C4 | C5 | Z1 | Z2 | Z3 | Z4 | Z5 | R1 | R2 | R3 | R4 | R5 |
| --- | --- | --- | --- | --- | --- | --- | --- | --- | --- | --- | --- | --- | --- | --- | --- |
| HbA1c (%) | 4.20 | 4.28 | 4.21 | 4.16 | 4.09 | 5.12 | 8.01 | 7.59 | 8.71 | 9.51 | 4.30 | 4.27 | 4.14 | 4.14 | 4.13 |

TABLE 8b

| comparison | ZDF rats Rosiglitazone treated, comparison to untreated ZDF rats, 20 weeks old | | | | |
|---|---|---|---|---|---|
| | Rosi 1 vs ZDF 1 | Rosi 2 vs ZDF 2 | Rosi 3 vs ZDF 3 | Rosi 4 vs ZDF 4 | Rosi 5 vs ZDF 5 |
| Fold change | 1.6 | 1.3 | 1.6 | 1.5 | 1.4 |

The invention claimed is:

1. A method of identifying anti-type 2 diabetes mellitus drugs, the method comprising:
   a) determining expression level of a PIM-3 nucleic acid molecule in a first adipocyte in the presence of a candidate compound wherein the PIM-3 nucleic acid molecule is selected from the group consisting of SEQ ID NO. 1, SEQ ID NO. 3, SEQ ID NO. 5 and SEQ ID NO. 7;
   b) determining expression level of the PIM-3 nucleic acid molecule in a second adipocyte in the absence of the candidate compound, and
   c) identifying an anti-type 2 diabetes mellitus drug by determining whether there is a difference in PIM-3 expression in the first adipocyte in the presence of the candidate compound compared to PIM-3 expression in the second adinocyte in the absence of candidate compound.

2. The method of claim 1 wherein the first and second adipocyte are differentiated 3T3-L1 cells.

* * * * *

UNITED STATES PATENT AND TRADEMARK OFFICE
CERTIFICATE OF CORRECTION

PATENT NO. : 7,629,126 B2  Page 1 of 2
APPLICATION NO. : 11/609,652
DATED : December 8, 2009
INVENTOR(S) : Marc Korn et al.

It is certified that error appears in the above-identified patent and that said Letters Patent is hereby corrected as shown below:

On the title page, under "Other Publications", in column 2, line 10, delete "Theronine" and insert -- Threonine --, therefor.

In column 5, line 36, delete "mRNIA" and insert -- mRNA --, therefor.

In column 6, line 36, after "of" delete "is".

In column 6, line 45, delete "polyclonial," and insert -- polyclonal, --, therefor.

In column 8, line 33, delete "matrix," and insert -- matrix. --, therefor.

In column 9, line 13, delete "polypeptde" and insert -- polypeptide --, therefor.

In column 10, line 65-66, delete "oligonucleoitides," and insert -- oligonucleotides, --, therefor.

In column 11, line 7, delete "decribed" and insert -- described --, therefor.

In column 11, line 8, delete "al" and insert -- a --, therefor.

In column 11, line 29, delete "CRNA" and insert -- cRNA --, therefor.

In column 11, line 29, delete "hydrolized" and insert -- hydrolyzed --, therefor.

In column 13, line 25, delete "Affimetrix" and insert -- Affymetrix --, therefor.

In column 13, line 66, delete "centrations" and insert -- (concentrations --, therefor.

In column 14, line 53, delete "outwith" and insert -- out with --, therefor.

In column 14, line 67, delete "results," and insert -- results --, therefor.

Signed and Sealed this

Third Day of August, 2010

David J. Kappos
*Director of the United States Patent and Trademark Office*

CERTIFICATE OF CORRECTION (continued)
U.S. Pat. No. 7,629,126 B2

In column 15, line 43, delete "1-10)were" and insert -- 1-10) were --, therefor.

In column 15, line 46, delete "1(animals" and insert -- 1 (animals --, therefor.

In column 16, line 43, delete "Affymetlrix" and insert -- Affymetrix --, therefor.

In column 16, line 45, delete "und" and insert -- and --, therefor.

In column 42, line 6, in Claim 1, delete "adinocyte" and insert -- adipocyte --, therefor.

SEQUENCE LISTING

<160> NUMBER OF SEQ ID NOS: 14

<210> SEQ ID NO 1
<211> LENGTH: 1973
<212> TYPE: DNA
<213> ORGANISM: Homo sapiens

<400> SEQUENCE: 1

```
gagggccgtc gcccgcgatg ctgctctcca agttcggctc cctggcgcac ctctgcgggc      60
ccggcggcgt ggaccacctc ccggtgaaga tcctgcagcc agccaaggcg acaaggagga     120
gcttcgagaa ggcgtaccag gtgggcgccg tgctgggtag cggcggcttc ggcacggtct     180
acgcgggtag ccgcatcgcc gacgggctcc cggtggctgt gaagcacgtg gtgaaggagc     240
gggtgaccga gtggggcagc ctgggcggcg cgaccgtgcc cctggaggtg gtgctgctgc     300
gcaaggtggg cgcggcgggc ggcgcgcgcg cgtcatccg cctgctggac tggttcgagc     360
ggcccgacgg cttcctgctg gtgctggagc ggcccgagcc ggcgcaggac ctcttcgact     420
ttatcacgga gcgcggcgcc ctggacgagc cgctggcgcg ccgcttcttc gcgcaggtgc     480
tggccgccgt gcgccactgc cacagctgcg gggtcgtgca ccgcgacatt aaggacgaaa     540
atctgcttgt ggacctgcgc tccggagagc tcaagctcat cgacttcggt tcgggtgcgc     600
tgctcaagga cacggtctac accgacttcg acggcacccg agtgtacagc cccccggagt     660
ggatccgcta ccaccgctac cacgggcgct cggccaccgt gtggtcgctg ggcgtgcttc     720
tctacgatat ggtgtgtggg gacatcccct tcgagcagga cgaggagatc ctccgaggcc     780
gcctgctctt ccggaggagg gtctctccag agtgccagca gctgatccgg tggtgcctgt     840
ccctgcggcc ctcagagcgg ccgtcgctgg atcagattgc ggcccatccc tggatgctgg     900
gggctgacgg gggcgccccg gagagctgtg acctgcggct gtgcaccctc gaccctgatg     960
acgtggccag caccacgtcc agcagcgaga gcttgtgagg agctgcacct gactgggagc    1020
taggggacca cctgccttgg ccagacctgg gacgccccca gccctgact ttttcctgcg     1080
tgggccgtct cctcctgcgg aagcagtgac ctctgacccc tggtgacctt cgctttgagt    1140
gcctttgaa cgctggtccc gcgggacttg gttttctcaa gctctgtctg tccaaagacg     1200
ctccggtcga ggtcccgcct gccctgggtg gatacttgaa ccccagacgc ccctctgtgc    1260
tgctgtgtcc ggaggcggcc ttcccatctg cctgcccacc cggagctctt tccgccggcg    1320
cagggtccca gcccacctc ccgccctcag tcctgcggtg tgcgtctggg cacgtcctgc     1380
acacacaatg caagtcctgg cctccgcgcc cgcccgccca cgcgagccgt accgccgcc      1440
aactctgtta tttatggtgt gacccctgg aggtgccctc ggcccaccgg ggctatttat      1500
tgtttaattt atttgttgag gttatttcct ctgagcagtc tgcctctccc aagccccagg    1560
ggacagtggg gaggcagggg aggggtggc tgtggtccag ggaccccagg ccctgattcc     1620
```

-continued

```
tgtgcctggc gtctgtcctg gccccgcctg tcagaagatg aacatgtata gtggctaact   1680 taagggagt gggtgaccct gacacttcca ggcactgtgc ccagggtttg ggttttaaat    1740
tattgacttt gtacagtctg cttgtgggct ctgaaagctg gggtggggcc agagcctgag   1800
cgtttaattt attcagtacc tgtgtttgtg tgaatgcggt gtgtgcaggc atcgcagatg   1860
ggggttcttt cagttcaaaa gtgagatgtc tggagatcat atttttttat acaggtattt   1920
caattaaaat gttttgtac atagtggaaa aaaaaaaaa aagggcggcc gcc            1973
```

<210> SEQ ID NO 2
<211> LENGTH: 326
<212> TYPE: PRT
<213> ORGANISM: Homo sapiens

<400> SEQUENCE: 2

```
Met Leu Leu Ser Lys Phe Gly Ser Leu Ala His Leu Cys Gly Pro Gly
1               5                   10                  15

Gly Val Asp His Leu Pro Val Lys Ile Leu Gln Pro Ala Lys Ala Asp
            20                  25                  30

Lys Glu Ser Phe Glu Lys Ala Tyr Gln Val Gly Ala Val Leu Gly Ser
        35                  40                  45

Gly Gly Phe Gly Thr Val Tyr Ala Gly Ser Arg Ile Ala Asp Gly Leu
    50                  55                  60

Pro Val Ala Val Lys His Val Lys Glu Arg Val Thr Glu Trp Gly
65                  70                  75                  80

Ser Leu Gly Gly Ala Thr Val Pro Leu Glu Val Val Leu Leu Arg Lys
                85                  90                  95

Val Gly Ala Ala Gly Gly Ala Arg Gly Val Ile Arg Leu Leu Asp Trp
            100                 105                 110

Phe Glu Arg Pro Asp Gly Phe Leu Leu Val Leu Glu Arg Pro Glu Pro
        115                 120                 125

Ala Gln Asp Leu Phe Asp Phe Ile Thr Glu Arg Gly Ala Leu Asp Glu
    130                 135                 140

Pro Leu Ala Arg Arg Phe Phe Ala Gln Val Leu Ala Ala Val Arg His
145                 150                 155                 160

Cys His Ser Cys Gly Val Val His Arg Asp Ile Lys Asp Glu Asn Leu
                165                 170                 175

Leu Val Asp Leu Arg Ser Gly Glu Leu Lys Leu Ile Asp Phe Gly Ser
            180                 185                 190

Gly Ala Leu Leu Lys Asp Thr Val Tyr Thr Asp Phe Asp Gly Thr Arg
        195                 200                 205

Val Tyr Ser Pro Pro Glu Trp Ile Arg Tyr His Arg Tyr His Gly Arg
    210                 215                 220

Ser Ala Thr Val Trp Ser Leu Gly Val Leu Leu Tyr Asp Met Val Cys
225                 230                 235                 240

Gly Asp Ile Pro Phe Glu Gln Asp Glu Glu Ile Leu Arg Gly Arg Leu
                245                 250                 255

Leu Phe Arg Arg Arg Val Ser Pro Glu Cys Gln Gln Leu Ile Arg Trp
            260                 265                 270

Cys Leu Ser Leu Arg Pro Ser Glu Arg Pro Ser Leu Asp Gln Ile Ala
        275                 280                 285

Ala His Pro Trp Met Leu Gly Ala Asp Gly Gly Ala Pro Glu Ser Cys
    290                 295                 300

Asp Leu Arg Leu Cys Thr Leu Asp Pro Asp Asp Val Ala Ser Thr Thr
```

Ser Ser Ser Glu Ser Leu
305 310 315 320
325

<210> SEQ ID NO 3
<211> LENGTH: 978
<212> TYPE: DNA
<213> ORGANISM: Homo sapiens

<400> SEQUENCE: 3

| | | | | | |
|---|---|---|---|---|---|
| atgctgctct | ccaagttcgg | ctccctggcg | cacctctgcg | ggcccggcgg | cgtggaccac | 60 |
| ctcccggtga | agatcctgca | gccagccaag | gcggacaagg | agagcttcga | gaaggcgtac | 120 |
| caggtgggcg | ccgtgctggg | tagcggcggc | ttcggcacgg | tctacgcggg | tagccgcatc | 180 |
| gccgacgggc | tcccggtggc | tgtgaagcac | gtggtgaagg | agcgggtgac | cgagtggggc | 240 |
| agcctgggcg | gcgcgaccgt | gcccctggag | gtggtgctgc | tgcgcaaggt | gggcgcggcg | 300 |
| ggcggcgcgc | gcggcgtcat | ccgcctgctg | gactggttcg | agcggcccga | cggcttcctg | 360 |
| ctggtgctgg | agcggcccga | gccggcgcag | gacctcttcg | actttatcac | ggagcgcggc | 420 |
| gccctggacg | agccgctggc | gcgccgcttc | ttcgcgcagg | tgctggccgc | cgtgcgccac | 480 |
| tgccacagct | gcggggtcgt | gcaccgcgac | attaaggacg | aaaatctgct | tgtggacctg | 540 |
| cgctccggag | agctcaagct | catcgacttc | ggttcgggtg | cgctgctcaa | ggacacggtc | 600 |
| tacaccgact | cgacggcac | ccgagtgtac | agcccccgg | agtggatccg | ctaccaccgc | 660 |
| taccacgggc | gctcggccac | cgtgtggtcg | ctgggcgtgc | ttctctacga | tatggtgtgt | 720 |
| ggggacatcc | ccttcgagca | ggacgaggag | atcctccgag | gccgcctgct | cttccggagg | 780 |
| agggtctctc | cagagtgcca | gcagctgatc | cggtggtgcc | tgtccctgcg | gccctcagag | 840 |
| cggccgtcgc | tggatcagat | tgcggcccat | ccctggatgc | tgggggctga | cggggggcgcc | 900 |
| ccggagagct | gtgacctgcg | gctgtgcacc | ctcgaccctg | atgacgtggc | cagcaccacg | 960 |
| tccagcagcg | agagcttg | | | | | 978 |

<210> SEQ ID NO 4
<211> LENGTH: 254
<212> TYPE: PRT
<213> ORGANISM: Artificial
<220> FEATURE:
<223> OTHER INFORMATION: Recombinant Plasmid

<400> SEQUENCE: 4

Tyr Gln Val Gly Ala Val Leu Gly Ser Gly Gly Phe Gly Thr Val Tyr
1               5                   10                  15

Ala Gly Ser Arg Ile Ala Asp Gly Leu Pro Val Ala Val Lys His Val
            20                  25                  30

Val Lys Glu Arg Val Thr Glu Trp Gly Ser Leu Gly Gly Ala Thr Val
        35                  40                  45

Pro Leu Glu Val Val Leu Leu Arg Lys Val Gly Ala Ala Gly Gly Ala
    50                  55                  60

Arg Gly Val Ile Arg Leu Leu Asp Trp Phe Glu Arg Pro Asp Gly Phe
65                  70                  75                  80

Leu Leu Val Leu Glu Arg Pro Glu Pro Ala Gln Asp Leu Phe Asp Phe
                85                  90                  95

Ile Thr Glu Arg Gly Ala Leu Asp Glu Pro Leu Ala Arg Arg Phe Phe
            100                 105                 110

Ala Gln Val Leu Ala Ala Val Arg His Cys His Ser Cys Gly Val Val

```
              115                 120                 125
His Arg Asp Ile Lys Asp Glu Asn Leu Leu Val Asp Leu Arg Ser Gly
    130                 135                 140

Glu Leu Lys Leu Ile Asp Phe Gly Ser Gly Ala Leu Leu Lys Asp Thr
145                 150                 155                 160

Val Tyr Thr Asp Phe Asp Gly Thr Arg Val Tyr Ser Pro Pro Glu Trp
                165                 170                 175

Ile Arg Tyr His Arg Tyr His Gly Arg Ser Ala Thr Val Trp Ser Leu
                180                 185                 190

Gly Val Leu Leu Tyr Asp Met Val Cys Gly Asp Ile Pro Phe Glu Gln
            195                 200                 205

Asp Glu Glu Ile Leu Arg Gly Arg Leu Leu Phe Arg Arg Arg Val Ser
    210                 215                 220

Pro Glu Cys Gln Gln Leu Ile Arg Trp Cys Leu Ser Leu Arg Pro Ser
225                 230                 235                 240

Glu Arg Pro Ser Leu Asp Gln Ile Ala Ala His Pro Trp Met
                245                 250

<210> SEQ ID NO 5
<211> LENGTH: 2236
<212> TYPE: DNA
<213> ORGANISM: Mus musculus

<400> SEQUENCE: 5
tgacactata gaaggtacgc ctgcaggtac cggtccggaa ttcccgggtc gacccacgcg      60
tccgcgccgc gcggctgccc cgctgagcgc tcggcctcgg ggccgtggga tccgccgcgc     120
tgtctgcggt caggaagacc gccctcccgc gtccttgccg gacgggtcag aggcggcacc     180
gcacgcgagg ccacccgcga tgctgctgtc caagttcggc tccctggcgc acctctgcgg     240
gcctggcggc gtggaccacc tcccagtgaa gatcctacag ccagccaagg ctgacaagga     300
gagcttcgag aaggtgtacc aggtgggcgc cgtgctgggc agcggcggct cggcacggt      360 ctacgcgggc agccgcatcg ccgacggact cccggtggct gtgaagcacg tggtgaagga     420
gcgggtgacc gagtggggca gtctcgcgg agtggccgtg ccctggagg tggtgctgct      480 gcgcaaggtg ggcgcggcgg gcggcgcgcg cggcgtcatc cgcttgctgg actggttcga     540
gcggcccgac ggcttcttgt tggtgctgga gcgacccgag ccggcacagg acctcttcga     600
cttcatcact gaacgaggcg ccctggacga gccgctggcg cgtcgcttct cgcgcaggt      660 gcttgccgct gtgcggcact gccacaattg tggggtcgtg caccgcgaca tcaaggacga     720
gaacctgctg gtggacctgc gctcgggaga gctgaagctc atcgacttcg gctcgggcgc     780
ggtgctcaag gacacggtct acactgactt tgatggcacc cgtgtgtaca gcccccagt a     840 gtggatccga tatcaccgat atcacgggcg gtctgccact gtgtggtctc tgggtgtact     900
gctctacgac atggtgtgtg gggacattcc ctttgagcag gatgaggaga tcttgcgcgg     960
caggctcttt ttccggagga gggtctcccc agagtgccag cagcttattg agtggtgtct    1020
ctccctgagg ccctcagaga ggccctccct ggaccaaatt gctgcccacc cctggatgct    1080
ggggacagag gggagcgttc agagaactg tgaccttcgg ctttgtgccc tggatactga    1140
cgacggagcc agtaccactt ccagcagtga gagcttgtga ggaggagaag gggcctgggc    1200
tcggcctagc cagcgctctc ccagaattga acactttctg cctgggatgt ctgctgcaaa    1260
agcagtgacc tctgacccct ggtgaccttt gctctcggca ccgggcctgt ttcctttgct    1320
ttgagtgcct ttttgaacgc tgctccacag ggcctgggtt ttcttgagct cttctgtcca    1380
```

```
aagatggctg cgggctaagc aaggtcctgc cctgggtgga tacttgaacc agagatcccg    1440
accctgctgc tccatctcag gaggcagcct tcctgaccaa gtgtgtttga catggagcgc    1500
cctgtggtgc ccacctccaa ccctccagtc tcctggtgtt catctgggca tgtctgcaca    1560
agcaatgcaa cgctgggcca ctgctgcccg tctgcctccc cggcacggca cggctccgca    1620
cgcaacctaa gcgtgccacc acggtctctt atttatggtg tgatcaccct ggagggcgcc    1680
cccgccctgc tggggctatt tattgtttaa tttatttgct gaggttcctc caagcaacca    1740
ccttctccag gcccctgggg tgttgaaagt caaatgtggc tgttgagtcc acagaccccc    1800
atcctaattc ctgcacctgg aggagttccc caaccccgt gtttgcggga ggaagcattt     1860
gtacagtggc taatttaagg ggagtgggag accctgtcac cctgagcact ctgcgctggg    1920
gaggggttta aattattgac cttgtacagt ctgcttgctg gctctgaaag ctggggttgg    1980
gggacagagt ctcaagccct taatttattt tagcagctgt gtttctgtga ccctggtgtg    2040
actaagcatc aggggtgggg ttgtataagt tcaaaagtgt gaaatgtctg aagatcatat    2100
tttttataca ggtatttcaa ttaaatgttt tggtatataa aaaaaaaaaa aaaaaaaaa     2160 aagggcggcc gctctagagg atccctcgag gggcccaagc ttacgcgtgc atgcgacgtc    2220
atagctctct ccctat                                                    2236
```

<210> SEQ ID NO 6
<211> LENGTH: 326
<212> TYPE: PRT
<213> ORGANISM: Mus musculus

<400> SEQUENCE: 6

```
Met Leu Leu Ser Lys Phe Gly Ser Leu Ala His Leu Cys Gly Pro Gly
1               5                   10                  15

Gly Val Asp His Leu Pro Val Lys Ile Leu Gln Pro Ala Lys Ala Asp
            20                  25                  30

Lys Glu Ser Phe Glu Lys Val Tyr Gln Val Gly Ala Val Leu Gly Ser
        35                  40                  45

Gly Gly Phe Gly Thr Val Tyr Ala Gly Ser Arg Ile Ala Asp Gly Leu
    50                  55                  60

Pro Val Ala Val Lys His Val Val Lys Glu Arg Val Thr Glu Trp Gly
65                  70                  75                  80

Ser Leu Gly Gly Val Ala Val Pro Leu Glu Val Val Leu Leu Arg Lys
                85                  90                  95

Val Gly Ala Ala Gly Gly Ala Arg Gly Val Ile Arg Leu Leu Asp Trp
            100                 105                 110

Phe Glu Arg Pro Asp Gly Phe Leu Leu Val Leu Glu Arg Pro Glu Pro
        115                 120                 125

Ala Gln Asp Leu Phe Asp Phe Ile Thr Glu Arg Gly Ala Leu Asp Glu
    130                 135                 140

Pro Leu Ala Arg Arg Phe Phe Ala Gln Val Leu Ala Ala Val Arg His
145                 150                 155                 160

Cys His Asn Cys Gly Val Val His Arg Asp Ile Lys Asp Glu Asn Leu
                165                 170                 175

Leu Val Asp Leu Arg Ser Gly Glu Leu Lys Leu Ile Asp Phe Gly Ser
            180                 185                 190

Gly Ala Val Leu Lys Asp Thr Val Tyr Thr Asp Phe Asp Gly Thr Arg
        195                 200                 205

Val Tyr Ser Pro Pro Glu Trp Ile Arg Tyr His Arg Tyr His Gly Arg
```

```
            210                 215                 220
Ser Ala Thr Val Trp Ser Leu Gly Val Leu Leu Tyr Asp Met Val Cys
225                 230                 235                 240

Gly Asp Ile Pro Phe Glu Gln Asp Glu Glu Ile Leu Arg Gly Arg Leu
                245                 250                 255

Phe Phe Arg Arg Arg Val Ser Pro Glu Cys Gln Gln Leu Ile Glu Trp
            260                 265                 270

Cys Leu Ser Leu Arg Pro Ser Glu Arg Pro Ser Leu Asp Gln Ile Ala
        275                 280                 285

Ala His Pro Trp Met Leu Gly Thr Glu Gly Ser Val Pro Glu Asn Cys
    290                 295                 300

Asp Leu Arg Leu Cys Ala Leu Asp Thr Asp Asp Gly Ala Ser Thr Thr
305                 310                 315                 320

Ser Ser Ser Glu Ser Leu
                325

<210> SEQ ID NO 7
<211> LENGTH: 978
<212> TYPE: DNA
<213> ORGANISM: Mus musculus

<400> SEQUENCE: 7
atgctgctgt ccaagttcgg ctccctggcg cacctctgcg ggcctggcgg cgtggaccac      60
ctcccagtga agatcctaca gccagccaag gctgacaagg agagcttcga aaggtgtac     120 caggtgggcg ccgtgctggg cagcggcggc ttcggcacgg tctacgcggg cagccgcatc    180
gccgacggac tcccggtggc cgtgaagcac gtggtgaagg gcgggtgac cgagtggggc     240 agtctcggcg gagtggccgt gccccctggag gtggtgctgc tgcgcaaggt gggcgcggcg   300
ggcggcgcgc gcggcgtcat ccgcttgctg gactggttcg agcggcccga cggcttcttg    360
ttggtgctgg agcgacccga gccggcacag gacctcttcg acttcatcac tgaacgaggc    420
gccctggacg agccgctggc gcgtcgcttc ttcgcgcagg tgcttgccgc tgtgcggcac    480
tgccacaatt gtggggtcgt gcaccgcgac atcaaggacg agaacctgct ggtggacctg    540
cgctcgggag agctgaagct catcgacttc ggctcgggcg cggtgctcaa ggacacggtc    600
tacactgact ttgatggcac ccgtgtgtac agccccccag agtggatccg atatcaccga    660
tatcacgggc ggtctgccac tgtgtggtct ctgggtgtac tgctctacga catggtgtgt    720
ggggacattc cctttgagca ggatgaggag atcttgcgcg gcaggctctt tttccggagg    780
agggtctccc cagagtgcca gcagcttatt gagtggtgtc tctccctgag gccctcagag    840 aggcctccc tggaccaaat tgctgcccac ccctggatgc tggggacaga ggggagcgtt    900
ccagagaact gtgaccttcg gctttgtgcc ctggatactg acgacggagc cagtaccact    960
tccagcagtg agagcttg                                                  978

<210> SEQ ID NO 8
<211> LENGTH: 254
<212> TYPE: PRT
<213> ORGANISM: Artificial
<220> FEATURE:
<223> OTHER INFORMATION: Eukaryotic Protein Kinase Domain

<400> SEQUENCE: 8

Tyr Gln Val Gly Ala Val Leu Gly Ser Gly Gly Phe Gly Thr Val Tyr
1               5                   10                  15

Ala Gly Ser Arg Ile Ala Asp Gly Leu Pro Val Ala Val Lys His Val
```

```
                    20                  25                  30
Val Lys Glu Arg Val Thr Glu Trp Gly Ser Leu Gly Gly Val Ala Val
             35                  40                  45

Pro Leu Glu Val Val Leu Leu Arg Lys Val Gly Ala Ala Gly Gly Ala
         50                  55                  60

Arg Gly Val Ile Arg Leu Leu Asp Trp Phe Glu Arg Pro Asp Gly Phe
65                  70                  75                  80

Leu Leu Val Leu Glu Arg Pro Glu Pro Ala Gln Asp Leu Phe Asp Phe
                 85                  90                  95

Ile Thr Glu Arg Gly Ala Leu Asp Glu Pro Leu Ala Arg Phe Phe
             100                 105                 110

Ala Gln Val Leu Ala Ala Val Arg His Cys His Asn Cys Gly Val Val
             115                 120                 125

His Arg Asp Ile Lys Asp Glu Asn Leu Leu Val Asp Leu Arg Ser Gly
             130                 135                 140

Glu Leu Lys Leu Ile Asp Phe Gly Ser Gly Ala Val Leu Lys Asp Thr
145                 150                 155                 160

Val Tyr Thr Asp Phe Asp Gly Thr Arg Val Tyr Ser Pro Pro Glu Trp
                 165                 170                 175

Ile Arg Tyr His Arg Tyr His Gly Arg Ser Ala Thr Val Trp Ser Leu
             180                 185                 190

Gly Val Leu Leu Tyr Asp Met Val Cys Gly Asp Ile Pro Phe Glu Gln
             195                 200                 205

Asp Glu Glu Ile Leu Arg Gly Arg Leu Phe Phe Arg Arg Arg Val Ser
210                 215                 220

Pro Glu Cys Gln Gln Leu Ile Glu Trp Cys Leu Ser Leu Arg Pro Ser
225                 230                 235                 240

Glu Arg Pro Ser Leu Asp Gln Ile Ala Ala His Pro Trp Met
                 245                 250

<210> SEQ ID NO 9
<211> LENGTH: 2133
<212> TYPE: DNA
<213> ORGANISM: Rattus norvegicus

<400> SEQUENCE: 9
cgctcggcca gctgccgtct acgggcttcc gcgcggccac cgggcaactg cgccgcgcgg    60
ctgccccact gagcgctcgg cctcggggcc gtgggatccg ccgcgctgtc tgcggtcagg   120
aagaccgccc tcccgcgtcc gtgccggacg ggtcagaggc ggcgccgcac gcgaggccac   180
ccgcgatgct gctgtccaag ttcggctccc tggcgcacct ctgcgggcct ggcggcgtgg   240
accacctccc agtgaagatc ctacagccag ccaaggcgga caaggagagc ttcgagaagg   300
tgtaccaggt gggcgccgtg ctcggcagcg gcggcttcgg cacggtctac gcgggcagcc   360
gcatcgccga cggactcccg gtggctgtga agcacgtggt gaaggagcgg gtgaccgagt   420
ggggcagtct cggcggaatg gccgtgcccc tggaggtggt gctgctgcgc aaggtgggcg   480
cggcgggcgg cgcgcgcggc gtcatccgcc tgctggactg gttcgagcgg cccgacggct   540
tcctgctggt gctggagcga cccgagccgg cacaggacct cttcgacttc atcactgaac   600
gcggcgccct ggacgagcct ctggctcgtc gcttcttcgc gcaggtgctc gccgctgtgc   660
ggcactgcca caattgtggg gtcgtgcacc gcgacatcaa ggacgagaac ctgctggtgg   720
acttgcgctc gggcgagctg aagctcatcg acttcggctc gggcgcggtg ctcaaggaca   780
cggtctacac tgactttgat ggcacccgtg tgtacagccc cccagagtgg atccggtatc   840
```

-continued

```
atcgatatca cgggcggtct gccactgtgt ggtctctggg tgtactgctc tacgacatgg     900
tgtgtgggga cattcccttt gagcaggatg aggagatctt gcgcggcagg ctcttttttcc    960
ggaggagggt ctccccagag tgccagcagc ttattgagtg gtgtctctcc ctgcggccct    1020
cagagaggcc ctcgctggac caaattgctg cccatccctg gatgctgggg acagagggca    1080
gcgttccaga gaactgtgac cttcggctct gtgccctgga tactgatgac ggagccagta    1140
ccacttccag cagtgagagc ttgtgaggag gaggaggggc ctggactcca cactgggggc    1200
ctgggctcag cctagccagc cctctcccag aatgaacatt ttctgcctgg gatgtctcct    1260
gcaaaagcag tgacctctga cccctggtga cctttgctct cggcaccggg cctgtttcct    1320
ttgctttgag tgccttttg aacgctgctc cacagggcct gggttttctt gagctcttct     1380
gtccaaagat ggctgcgggc taagcaaggt cccgcctgcc ctgggtggat acttgaaccc    1440
gagaccctac cctgctgctc catcttgcgg cagccttcct gaccaagtgt gtttgacatg    1500
gagcgccctg tggtgcccac ctccaaccct ccagtctcct ggtcttcgtc tgggcatgtc    1560
tgcacaagca atgcaacgct gggccactgc tgcccgcctg cctccctggc accgcacgca    1620
acgagcgtgc cacggtctct tatttatggt gtgatcaccc tggagggcgc ccctgccctg    1680
ctggggctat ttattgttta atttatttgc tgaggttact tcctccaagc aaccaccttc    1740
tccaggcccc tggggtgttc aggaaagcca agggtggccg ttcagtccac agacggcatc    1800
ctggttcctg cacctgcagt aggtccctaa ccccatgttt gtgggaggag gaatttgtac    1860
agtggctaat ttaaggggag tgggagaccc tgtcaccctg gcactctgc gctggggagg     1920
gggtttaaat tattgacctt gtacagtctg cttgctggct ctgaaagctg gggtggggga    1980
cagagtctca agcccttaat ttattttagc aactgtgttc tgtgaccctg gtgtgagtag    2040
gcatcagggg tggggttgta taagttcaaa agtgtgaaat gtctggagat catatttttt    2100
atacaggtat ttcaattaaa tgttttggta tat                                2133
```

<210> SEQ ID NO 10
<211> LENGTH: 326
<212> TYPE: PRT
<213> ORGANISM: Rattus norvegicus

<400> SEQUENCE: 10

```
Met Leu Leu Ser Lys Phe Gly Ser Leu Ala His Leu Cys Gly Pro Gly
 1               5                  10                  15

Gly Val Asp His Leu Pro Val Lys Ile Leu Gln Pro Ala Lys Ala Asp
             20                  25                  30

Lys Glu Ser Phe Glu Lys Val Tyr Gln Val Gly Ala Val Leu Gly Ser
         35                  40                  45

Gly Gly Phe Gly Thr Val Tyr Ala Gly Ser Arg Ile Ala Asp Gly Leu
     50                  55                  60

Pro Val Ala Val Lys His Val Val Lys Glu Arg Val Thr Glu Trp Gly
 65                  70                  75                  80

Ser Leu Gly Gly Met Ala Val Pro Leu Glu Val Val Leu Leu Arg Lys
                 85                  90                  95

Val Gly Ala Ala Gly Gly Ala Arg Gly Val Ile Arg Leu Leu Asp Trp
            100                 105                 110

Phe Glu Arg Pro Asp Gly Phe Leu Leu Val Leu Glu Arg Pro Glu Pro
        115                 120                 125

Ala Gln Asp Leu Phe Asp Phe Ile Thr Glu Arg Gly Ala Leu Asp Glu
    130                 135                 140
```

Pro Leu Ala Arg Arg Phe Phe Ala Gln Val Leu Ala Val Arg His
145                 150                 155                 160

Cys His Asn Cys Gly Val Val His Arg Asp Ile Lys Asp Glu Asn Leu
                165                 170                 175

Leu Val Asp Leu Arg Ser Gly Glu Leu Lys Leu Ile Asp Phe Gly Ser
            180                 185                 190

Gly Ala Val Leu Lys Asp Thr Val Tyr Thr Asp Phe Asp Gly Thr Arg
        195                 200                 205

Val Tyr Ser Pro Pro Glu Trp Ile Arg Tyr His Arg Tyr His Gly Arg
    210                 215                 220

Ser Ala Thr Val Trp Ser Leu Gly Val Leu Leu Tyr Asp Met Val Cys
225                 230                 235                 240

Gly Asp Ile Pro Phe Glu Gln Asp Glu Glu Ile Leu Arg Gly Arg Leu
                245                 250                 255

Phe Phe Arg Arg Arg Val Ser Pro Glu Cys Gln Gln Leu Ile Glu Trp
            260                 265                 270

Cys Leu Ser Leu Arg Pro Ser Glu Arg Pro Ser Leu Asp Gln Ile Ala
        275                 280                 285

Ala His Pro Trp Met Leu Gly Thr Glu Gly Ser Val Pro Glu Asn Cys
    290                 295                 300

Asp Leu Arg Leu Cys Ala Leu Asp Thr Asp Gly Ala Ser Thr Thr
305                 310                 315                 320

Ser Ser Ser Glu Ser Leu
                325

<210> SEQ ID NO 11
<211> LENGTH: 323
<212> TYPE: PRT
<213> ORGANISM: Xenopus laevis

<400> SEQUENCE: 11

Met Leu Leu Ser Lys Phe Gly Ser Leu Ala His Ile Cys Asn Pro Ser
1               5                   10                  15

Asn Met Glu His Leu Pro Val Lys Ile Leu Gln Pro Val Lys Val Asp
                20                  25                  30

Lys Glu Pro Phe Glu Lys Val Tyr Gln Val Gly Ser Val Val Ala Ser
            35                  40                  45

Gly Gly Phe Gly Thr Val Tyr Ser Asp Ser Arg Ile Ala Asp Gly Gln
        50                  55                  60

Pro Val Ala Val Lys His Val Ala Lys Glu Arg Val Thr Glu Trp Gly
65                  70                  75                  80

Thr Leu Asn Gly Val Met Val Pro Leu Glu Ile Val Leu Leu Lys Lys
                85                  90                  95

Val Pro Thr Ala Phe Arg Gly Val Ile Asn Leu Leu Asp Trp Tyr Glu
            100                 105                 110

Arg Pro Asp Ala Phe Leu Ile Val Met Glu Arg Pro Glu Pro Val Lys
        115                 120                 125

Asp Leu Phe Asp Tyr Ile Thr Glu Lys Gly Pro Leu Asp Glu Asp Thr
    130                 135                 140

Ala Arg Gly Phe Phe Arg Gln Val Leu Glu Ala Val Arg His Cys Tyr
145                 150                 155                 160

Asn Cys Gly Val Val His Arg Asp Ile Lys Asp Glu Asn Leu Leu Val
                165                 170                 175

Asp Thr Arg Asn Gly Glu Leu Lys Leu Ile Asp Phe Gly Ser Gly Ala

-continued

```
                180                 185                 190
Leu Leu Lys Asp Thr Val Tyr Thr Asp Phe Asp Gly Thr Arg Val Tyr
            195                 200                 205

Ser Pro Pro Glu Trp Val Arg Tyr His Arg Tyr His Gly Arg Ser Ala
        210                 215                 220

Thr Val Trp Ser Leu Gly Val Leu Leu Tyr Asp Met Val Tyr Gly Asp
225                 230                 235                 240

Ile Pro Phe Glu Gln Asp Glu Ile Val Arg Val Arg Leu Cys Phe
                245                 250                 255

Arg Arg Arg Ile Ser Thr Glu Cys Gln Gln Leu Ile Lys Trp Cys Leu
            260                 265                 270

Ser Leu Arg Pro Ser Asp Arg Pro Thr Leu Glu Gln Ile Phe Asp His
        275                 280                 285

Pro Trp Met Cys Lys Cys Asp Leu Val Lys Ser Glu Asp Cys Asp Leu
        290                 295                 300

Arg Leu Arg Thr Ile Asp Asn Asp Ser Ser Thr Ser Ser Ser Asn
305                 310                 315                 320

Glu Ser Leu

<210> SEQ ID NO 12
<211> LENGTH: 313
<212> TYPE: PRT
<213> ORGANISM: Rattus norvegicus

<400> SEQUENCE: 12

Met Leu Leu Ser Lys Ile Asn Ser Leu Ala His Leu Arg Ala Ala Pro
1               5                   10                  15

Cys Asn Asp Leu His Ala Asn Lys Leu Ala Pro Gly Lys Glu Lys Glu
            20                  25                  30

Pro Leu Glu Ser Gln Tyr Gln Val Gly Pro Leu Leu Gly Ser Gly Gly
        35                  40                  45

Phe Gly Ser Val Tyr Ser Gly Ile Arg Val Ala Asp Asn Leu Pro Val
    50                  55                  60

Ala Ile Lys His Val Glu Lys Asp Arg Ile Ser Asp Trp Gly Glu Leu
65                  70                  75                  80

Pro Asn Gly Thr Arg Val Pro Met Glu Val Val Leu Leu Lys Lys Val
                85                  90                  95

Ser Ser Gly Phe Ser Gly Val Ile Arg Leu Leu Asp Trp Phe Glu Arg
            100                 105                 110

Pro Asp Ser Phe Val Leu Ile Leu Glu Arg Pro Glu Pro Val Gln Asp
        115                 120                 125

Leu Phe Asp Phe Ile Thr Glu Arg Gly Ala Leu Gln Glu Glu Leu Ala
        130                 135                 140

Arg Ser Phe Phe Trp Gln Val Leu Glu Ala Val Arg His Cys His Asn
145                 150                 155                 160

Cys Gly Val Leu His Arg Asp Ile Lys Asp Glu Asn Ile Leu Ile Asp
                165                 170                 175

Leu Asn Arg Gly Glu Leu Lys Leu Ile Asp Phe Gly Ser Gly Ala Leu
            180                 185                 190

Leu Lys Asp Thr Val Tyr Thr Asp Phe Asp Gly Thr Arg Val Tyr Ser
        195                 200                 205

Pro Pro Glu Trp Ile Arg Tyr His Arg Tyr His Gly Arg Ser Ala Ala
        210                 215                 220

Val Trp Ser Leu Gly Ile Leu Leu Tyr Asp Met Val Cys Gly Asp Ile
```

-continued

```
               225                 230                 235                 240
Pro Phe Glu His Asp Glu Ile Val Lys Gly Gln Val Tyr Phe Arg
                245                 250                 255
Gln Arg Val Ser Ser Glu Cys Gln His Leu Ile Arg Trp Cys Leu Ser
            260                 265                 270
Leu Arg Pro Ser Asp Arg Pro Ser Phe Glu Glu Ile Gln Asn His Pro
        275                 280                 285
Trp Met Gln Asp Val Leu Leu Pro Gln Ala Thr Ala Glu Ile His Leu
    290                 295                 300
His Ser Leu Ser Pro Ser Pro Ser Lys
305                 310

<210> SEQ ID NO 13
<211> LENGTH: 313
<212> TYPE: PRT
<213> ORGANISM: Homo sapiens

<400> SEQUENCE: 13

Met Leu Leu Ser Lys Ile Asn Ser Leu Ala His Leu Arg Ala Ala Pro
1               5                   10                  15
Cys Asn Asp Leu His Ala Thr Lys Leu Ala Pro Gly Lys Glu Lys Glu
                20                  25                  30
Pro Leu Glu Ser Gln Tyr Gln Val Gly Pro Leu Leu Gly Ser Gly Gly
            35                  40                  45
Phe Gly Ser Val Tyr Ser Gly Ile Arg Val Ser Asp Asn Leu Pro Val
    50                  55                  60
Ala Ile Lys His Val Glu Lys Asp Arg Ile Ser Asp Trp Gly Glu Leu
65                  70                  75                  80
Pro Asn Gly Thr Arg Val Pro Met Glu Val Val Leu Leu Lys Lys Val
                85                  90                  95
Ser Ser Gly Phe Ser Gly Val Ile Arg Leu Leu Asp Trp Phe Glu Arg
            100                 105                 110
Pro Asp Ser Phe Val Leu Ile Leu Glu Arg Pro Glu Pro Val Gln Asp
        115                 120                 125
Leu Phe Asp Phe Ile Thr Glu Arg Gly Ala Leu Gln Glu Glu Leu Ala
    130                 135                 140
Arg Ser Phe Phe Trp Gln Val Leu Glu Ala Val Arg His Cys His Asn
145                 150                 155                 160
Cys Gly Val Leu His Arg Asp Ile Lys Asp Glu Asn Ile Leu Ile Asp
                165                 170                 175
Leu Asn Arg Gly Glu Leu Lys Leu Ile Asp Phe Gly Ser Gly Ala Leu
            180                 185                 190
Leu Lys Asp Thr Val Tyr Thr Asp Phe Asp Gly Thr Arg Val Tyr Ser
        195                 200                 205
Pro Pro Glu Trp Ile Arg Tyr His Arg Tyr His Gly Arg Ser Ala Ala
    210                 215                 220
Val Trp Ser Leu Gly Ile Leu Leu Tyr Asp Met Val Cys Gly Asp Ile
225                 230                 235                 240
Pro Phe Glu His Asp Glu Ile Ile Arg Gly Gln Val Phe Phe Arg
                245                 250                 255
Gln Arg Val Ser Ser Glu Cys Gln His Leu Ile Arg Trp Cys Leu Ala
            260                 265                 270
Leu Arg Pro Ser Asp Arg Pro Thr Phe Glu Glu Ile Gln Asn His Pro
        275                 280                 285
```

```
Trp Met Gln Asp Val Leu Leu Pro Gln Glu Thr Ala Glu Ile His Leu
    290                 295                 300
His Ser Leu Ser Pro Gly Pro Ser Lys
305                 310
```

<210> SEQ ID NO 14
<211> LENGTH: 313
<212> TYPE: PRT
<213> ORGANISM: Mus musculus

<400> SEQUENCE: 14

```
Met Leu Leu Ser Lys Ile Asn Ser Leu Ala His Leu Arg Ala Arg Pro
1               5                   10                  15
Cys Asn Asp Leu His Ala Thr Lys Leu Ala Pro Gly Lys Glu Lys Glu
                20                  25                  30
Pro Leu Glu Ser Gln Tyr Gln Val Gly Pro Leu Leu Gly Ser Gly Gly
            35                  40                  45
Phe Gly Ser Val Tyr Ser Gly Ile Arg Val Ala Asp Asn Leu Pro Val
    50                  55                  60
Ala Ile Lys His Val Glu Lys Asp Arg Ile Ser Asp Trp Gly Glu Leu
65                  70                  75                  80
Pro Asn Gly Thr Arg Val Pro Met Glu Val Val Leu Leu Lys Lys Val
                85                  90                  95
Ser Ser Asp Phe Ser Gly Val Ile Arg Leu Leu Asp Trp Phe Glu Arg
                100                 105                 110
Pro Asp Ser Phe Val Leu Ile Leu Glu Arg Pro Glu Pro Val Gln Asp
            115                 120                 125
Leu Phe Asp Phe Ile Thr Glu Arg Gly Ala Leu Gln Glu Asp Leu Ala
    130                 135                 140
Arg Gly Phe Phe Trp Gln Val Leu Glu Ala Val Arg His Cys His Asn
145                 150                 155                 160
Cys Gly Val Leu His Arg Asp Ile Lys Asp Glu Asn Ile Leu Ile Asp
                165                 170                 175
Leu Ser Arg Gly Glu Ile Lys Leu Ile Asp Phe Gly Ser Gly Ala Leu
                180                 185                 190
Leu Lys Asp Thr Val Tyr Thr Asp Phe Asp Gly Thr Arg Val Tyr Ser
            195                 200                 205
Pro Pro Glu Trp Ile Arg Tyr His Arg Tyr His Gly Arg Ser Ala Ala
    210                 215                 220
Val Trp Ser Leu Gly Ile Leu Leu Tyr Asp Met Val Cys Gly Asp Ile
225                 230                 235                 240
Pro Phe Glu His Asp Glu Glu Ile Ile Lys Gly Gln Val Phe Phe Arg
                245                 250                 255
Gln Thr Val Ser Ser Glu Cys Gln His Leu Ile Lys Trp Cys Leu Ser
                260                 265                 270
Leu Arg Pro Ser Asp Arg Pro Ser Phe Glu Glu Ile Arg Asn His Pro
            275                 280                 285
Trp Met Gln Gly Asp Leu Leu Pro Gln Ala Ala Ser Glu Ile His Leu
    290                 295                 300
His Ser Leu Ser Pro Gly Ser Ser Lys
305                 310
```